United States Patent
Blurton et al.

(10) Patent No.: US 6,180,630 B1
(45) Date of Patent: Jan. 30, 2001

(54) TRICYCLIC PYRAZOLO-PYRIDAZINONE ANALOGUES AS GAGA-A RECEPTOR LIGANDS

(75) Inventors: Peter Blurton, Welwyn Garden; Stephen Robert Fletcher, Bishops Stortford, both of (GB)

(73) Assignee: Merck Sharp & Dohme Limited, Hoddeshon (GB)

(*) Notice: Under 35 U.S.C. 154(b), the term of this patent shall be extended for 0 days.

(21) Appl. No.: 09/445,613

(22) PCT Filed: Jun. 17, 1998

(86) PCT No.: PCT/GB98/01774

§ 371 Date: Dec. 8, 1999

§ 102(e) Date: Dec. 8, 1999

(87) PCT Pub. No.: WO99/00391

PCT Pub. Date: Jan. 7, 1999

(30) Foreign Application Priority Data

Jun. 27, 1997 (GB) .................................... 9713707

(51) Int. Cl.[7] .................. A61K 31/502; A61P 25/08; A61P 25/22; C07D 487/04
(52) U.S. Cl. .............................. 514/248; 544/234
(58) Field of Search .................. 544/234; 514/248

(56) References Cited

U.S. PATENT DOCUMENTS 4,591,589  5/1986  Gasc et al. .................. 544/236
4,602,014  7/1986  Yokyama ..................... 546/82

FOREIGN PATENT DOCUMENTS 0 168 350 A2  1/1986  (EP).
2 166 439     5/1986  (GB).

OTHER PUBLICATIONS

Bayley, et al., *J. Pschopharmacol.*, 10: 206–213 (1996).
Bristow, et al., *J. Pharmacol. Exp. Ther.*, 279: 492–501 (1996).
Dawson, et al., *Psychopharmacology*, 121: 109–117 (1995).
Wafford, et al., *Mol. Pharmacol.*, 50: 670–678 (1996).

*Primary Examiner*—Mukund J. Shah
*Assistant Examiner*—Venkataraman Balasubramanian
(74) *Attorney, Agent, or Firm*—Shu M. Lee; David L. Rose

(57) ABSTRACT

Pyrazolo[4,3-c]pyridazin-3-one analogues, represented by

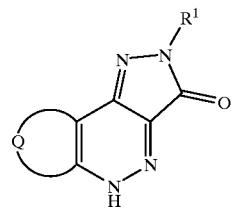

are selective ligands for $GABA_A$ receptors, in particular having high affinity for the α2 and/or α3 subunit thereof, are useful in the treatment of anxiety and convulsions.

9 Claims, No Drawings

TRICYCLIC PYRAZOLO-PYRIDAZINONE ANALOGUES AS GAGA-A RECEPTOR LIGANDS

The present invention relates to a class of fused tricyclic compounds based on a substituted pyrazolo-pyridazine moiety, and to their use in therapy. More particularly, this invention is concerned with tricyclic pyrazolo[4,3-c]pyridazin-3-one analogues which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta \gamma 2/3$, $\alpha 2\beta \gamma 1$, $\alpha 5\beta 3\gamma 2/3$, $\alpha 6\beta \gamma 2$, $\alpha 6\beta \delta$ and $\alpha 4\beta \delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain ($\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

U.S. Pat. No. 4,591,589 and GB-A-2166439 describe various classes of substituted pyrazolo[4,3-c]cinnolin-3-one derivatives. The compounds described in GB-A-2166439 are stated to be useful as psychotropic agents. The compounds described in U.S. Pat. No. 4,591,589 are stated to be useful for relieving anxiety. There is, however, no disclosure nor any suggestion in either of these publications of the compounds according to the present invention wherein the pyridazine ring of a pyrazolo[4,3-c]pyridazin-3-one moiety is fused to an alkylene chain.

U.S. Pat. No. 4,602,014 relates to a family of substituted pyrazolo[3,4-d]pyridin-3-one derivatives wherein the pyridine ring thereof is fused inter alia to an alkylene chain.

These compounds are stated therein to be benzodiazepine receptor ligands having nervous system regulatory activity, including anxiomodulating activity. However, there is no disclosure nor any suggestion anywhere in U.S. Pat. No. 4,602,014 of the fused tricyclic pyrazolo[4,3-c]pyridazin-3-one analogues in accordance with the present invention.

The present invention provides a class of tricyclic pyrazolo-pyridazine analogues which possess desirable binding properties at various $GABA_A$ receptor subtypes. The compounds in accordance with the present invention have good affinity as ligands for the $\alpha 2$ and/or $\alpha 3$ subunit of the human $GABA_A$ receptor. The compounds of this invention may interact more favourably with the $\alpha 2$ and/or $\alpha 3$ subunit than with the $\alpha 1$ subunit. Desirably, the compounds of the invention will exhibit functional selectivity in terms of a selective efficacy for the $\alpha 2$ and/or $\alpha 3$ subunit relative to the $\alpha 1$ subunit.

The compounds of the present invention are $GABA_A$ receptor subtype ligands having a binding affinity ($K_i$) for the $\alpha 2$ and/or $\alpha 3$ subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the $\alpha 2$ and/or $\alpha 3$ subunit relative to the $\alpha 1$ subunit. However, compounds which are not selective in terms of their binding affinity for the $\alpha 2$ and/or $\alpha 3$ subunit relative to the $\alpha 1$ subunit are also encompassed within the scope of the present invention; such compounds will desirably exhibit functional selectivity in terms of a selective efficacy for the $\alpha 2$ and/or $\alpha 3$ subunit relative to the $\alpha 1$ subunit.

The present invention provides a compound of formula I, or a salt or prodrug thereof:

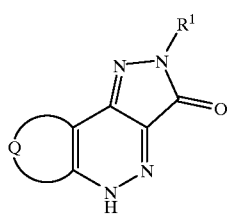

wherein

Q represents —$(CH_2)_n$—;

n is 3, 4, 5 or 6; and $R^1$ represents aryl or heteroaryl, either of which groups may be optionally substituted.

The group $R^1$ may be unsubstituted or substituted by one or more, preferably one or two, substituents. Examples of optional substituents on the group $R^1$ include $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonyl, $C_{2-6}$ alkoxycarbonyl, halogen, cyano and trifluoromethyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl and dimethylallyl groups.

The expression "$C_{2-6}$ alkynyl" as used herein refers to straight-chained and branched alkynyl groups containing from 2 to 6 carbon atoms. Typical examples include ethynyl and propargyl groups.

Particular $C_{3-7}$ cycloalkyl groups include cyclopropyl and cyclohexyl.

Particular aryl groups include phenyl and naphthyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, Q represents —(CH$_2$)$_n$— in which n is 4 or 5.

Suitably, the group R$^1$ represents phenyl or pyridinyl, either unsubstituted or substituted by one or more optional substituents selected typically from C$_{1-6}$ alkyl, C$_{1-6}$ alkoxy and halogen.

Particular values of R$^1$ include phenyl, methylphenyl, dimethylphenyl, ethylphenyl, isopropyl-phenyl, methoxyphenyl, ethoxyphenyl, fluorophenyl, difluorophenyl, chlorophenyl, pyridinyl and methylpyridinyl.

A particular sub-class of compounds according to the invention is represented by the compounds of formula II, and salts and prodrugs thereof:

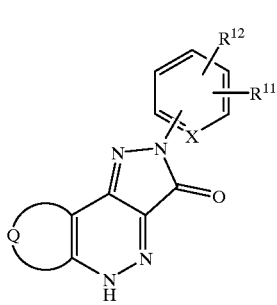

(II)

wherein

Q is as defined above with reference to formula I;

X represents CH or nitrogen; and

R$^{11}$ and R$^{12}$ independently represent hydrogen, C$_{1-6}$ alkyl, C$_{1-6}$ alkoxy, C$_{1-6}$ alkylsulphonyl, C$_{2-6}$ alkylcarbonyl, halogen, cyano or trifluoromethyl.

Suitably, R$^{11}$ represents hydrogen, C$_{1-6}$ alkyl, C$_{1-6}$ alkoxy or halogen. Particular values of R$^{11}$ include hydrogen, methyl, ethyl, isopropyl, methoxy, ethoxy, fluoro and chloro.

Suitably, R$^{12}$ represents hydrogen, C$_{1-6}$ alkyl or halogen. Particular values of R$^{12}$ include hydrogen, methyl and fluoro, especially hydrogen.

Specific compounds within the scope of the present invention include:

2-(4-methoxyphenyl)-2,5,6,7,8,9-hexahydropyrazolo[4,3-c]cinnolin-3-one;

2-(4-fluorophenyl)-2,5,6,7,8,9-hexahydropyrazolo[4,3-c]cinnolin-3-one;

2-(4-methylphenyl)-2,5,6,7,8,9-hexahydropyrazolo[4,3-c]cinnolin-3-one;

2-(3-chlorophenyl)-2,5,6,7,8,9-hexahydropyrazolo[4,3-c]cinnolin-3-one;

2-(2-fluorophenyl)-2,5,6,7,8,9-hexahydropyrazolo[4,3-c]cinnolin-3-one;

2-(pyridin-2-yl)-2,5,6,7,8,9-hexahydropyrazolo[4,3-c]cinnolin-3-one;

2-((4-ethylphenyl)-2,5,6,7,8,9-hexahydropyrazolo[4,3-c]cinnolin-3-one;

2-(2,4-difluorophenyl)-2,5,6,7,8,9-hexahydropyrazolo[4,3-c]cinnolin-3-one;

2-(3,4-dimethylphenyl)-2,5,6,7,8,9-hexahydropyrazolo[4,3-c]cinnolin-3-one;

2-(3-methylphenyl)-2,5,6,7,8,9-hexahydropyrazolo[4,3-c]cinnolin-3-one;

2-(3-fluorophenyl)-2,5,6,7,8,9-hexahydropyrazolo[4,3-c]cinnolin-3-one;

2-(4-isopropylphenyl)-2,5,6,7,8,9-hexahydropyrazolo[4,3-c]cinnolin-3-one;

2-(4-ethoxyphenyl)-2,5,6,7,8,9-hexahydropyrazolo[4,3-c]cinnolin-3-one;

2-(4-chyorophenyl)-2,5,6,7,8,9-hexahydropyrazolo[4,3-c]cinnolin-3-one;

2-(4-methoxyphenyl)-2,5,6,7,8,9,10-heptahydrocyclohepta[c]pyrazolo[4,3-c]pyridazin-3-one;

2-(4-methylphenyl)-2,5,6,7,8,9,10-heptahydrocyclohepta[c]pyrazolo[4,3-c]pyridazin-3-one;

2-(4-chlorophenyl)-2,5,6,7,8,9,10-heptahydrocyclohepta[c]pyrazolo[4,3-c]pyridazin-3-one;

2-(4-fluorophenyl)-2,5,6,7,8,9,10-heptahydrocyclohepta[c]pyrazolo[4,3-c]pyridazin-3-one;

2-(3-methoxyphenyl)-2,5,6,7,8,9,10-heptahydrocyclohepta[c]pyrazolo[4,3-c]pyridazin-3-one;

2-(pyridin-2-yl)-2,5,6,7,8,9,10-heptahydrocyclohepta[c]pyrazolo[4,3-c]pyridazin-3-one;

2-(4-methylpyridin-2-yl)-2,5,6,7,8,9,10-heptahydrocyclohepta[c]pyrazolo-[4,3-c]pyridazin-3-one;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity (K$_i$) of the compounds according to the present invention for the α3 subunit of the human GABA$_A$ receptor is conveniently as measured in the assay described hereinbelow. The α3 subunit binding affinity (K$_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA EC$_{20}$ response in stably transfected recombinant cell lines expressing the α3 subunit of the human GABA$_A$ receptor. Moreover, the compounds of the invention will ideally elicit at most a 30%, preferably at most a 20%, and more preferably at most a 10%, potentiation of the GABA EC$_{20}$ response in stably transfected recombinant cell lines expressing the α1 subunit of the human GABA$_A$ receptor.

The potentiation of the GABA EC$_{20}$ response in stably transfected cell lines expressing the α3 and α1 subunits of the human GABA$_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk$^-$ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–15 213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a hydrazine derivative of formula IV, or an acid addition salt thereof.

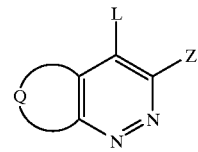

(III)

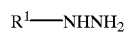

(IV)

wherein Q and $R^1$ are as defined above, L represents a readily displaceable group, and Z represents a reactive carboxylate moiety.

The acid addition salt of the hydrazine derivative of formula IV is suitably a mineral acid addition salt, typically the hydrochloride salt.

The readily displaceable group L in the compound of formula III is suitably a halogen atom, e.g. chloro.

Suitable values for the reactive carboxylate moiety Z include esters, for example $C_{1-4}$ alkyl esters; acid anhydrides, including mixed anhydrides with $C_{1-4}$ alkanoic acids; acid halides, for example acid chlorides; and acylimidazoles. Suitably, Z represents ethoxycarbonyl.

The reaction between compounds III and IV may conveniently be carried out under basic conditions in a suitable solvent, e.g. sodium carbonate or N,N-diisopropylethylamine (Hünig's base) in xylene.

A typical intermediate of formula III wherein the readily displaceable group L is chloro may conveniently be prepared by treating the compound of formula V:

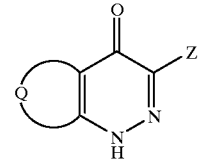

(V)

wherein Q and Z are as defined above; with p-toluenesulphonyl chloride, advantageously in the presence of lithium chloride and pyridine.

The reaction is conveniently effected in an inert solvent such as dichloromethane, typically at the reflux temperature of the solvent.

In an alternative procedure, the compounds according to the invention wherein Q represents —$(CH_2)_4$— may be prepared by a process which comprises reducing a compound of formula VI:

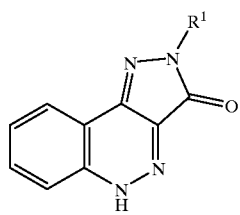

(VI)

wherein R¹ is as defined above.

The reaction is conveniently brought about by treating the compound of formula VI with hydrogen in the presence of a hydrogenation catalyst such as platinum oxide, or palladium on charcoal, typically in the presence of trifluoroacetic acid.

The intermediates of formula VI above may be prepared by methods analogous to those described in U.S. Pat. No. 4,591,589 and GB-A-2166439.

Where they are not commercially available, the starting materials of formula IV and V may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [³H]-flumazenil to the benzodiazepine binding site of human $GABA_A$ receptors containing the α2 or α3 subunit stably expressed in Ltk⁻ cells.

Reagents

Phosphate buffered saline (PBS).

Assay buffer: 10 mM $KH_2PO_4$, 100 mM KCl, pH 7.4 at room temperature.

[³H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [³H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [³H]-flumazenil from the α2 and/or α3 subunit of the human $GABA_A$ receptor of 100 nM or less.

EXAMPLE 1

2-(4-Methoxyphenyl)-2,5,6,7,8,9-hexahydropyrazolo[4,3-c]cinnolin-3-one

4-Oxo-1,4,5,6,7,8-hexahydrocinnoline-3-carboxylic acid ethyl ester

To 4-oxo-1,4-dihydrocinnoline-3-carboxylic acid ethyl ester (4.5 g) dissolved in trifluoroacetic acid (20 ml) was added platinum oxide (0.2 g). The reaction mixture was hydrogenated at 50 psi until no further uptake of hydrogen was observed. The catalyst was collected by filtration, the filtrate was poured onto ice, the pH was raised to pH6 with base, the resulting precipitate was collected by filtration, washed with water and dried to give a solid (2.8 g, 61%). $\delta_H$ (250 MHz; DMSO-$d_6$) 1.26 (3H, t, J=7 Hz, $CH_3$), 1.68 (4H, m, $CH_2$), 2.33 (2H, t, J=5.5 Hz, $CH_2$), 2.62 (2H, t, J=5.5 Hz, $CH_2$), 4.25 (2H, t, J=7 Hz, $CH_2$), 13.19 (1H, br s, NH), m/z (ESP+) 223 (MH⁺).

4-Chloro-5,6,7,8-tetrahydrocinnoline-3-carboxylic acid ethyl ester

To a slurry of 4-oxo-1,4,5,6,7,8-hexahydrocinnoline-3-carboxylic acid ethyl ester (1 g), lithium chloride (0.19 g) and pyridine (0.36 ml) in dichloromethane (30 ml) was added p-toluenesulphonyl chloride (0.85 g). The reaction mixture was heated at reflux for 20 h. The solid was collected by filtration, and the filtrate was evaporated under reduced pressure. The residue was purified by flash chromatography using a gradient elution: $CH_2Cl_2$ (500 ml), $CH_2Cl_2$/MeOH 99:1 (500 ml), $CH_2Cl_2$/MeOH 98:2 (1 liter). The appropriate fractions were combined and evaporated under reduced pressure to give a solid (0.65 g, 61%). $\delta_H$ (360 MHz; $CDCl_3$) 1.44 (3H, t, J=7 Hz, $CH_3$), 1.89 (4H, m, $CH_2$), 2.85 (2H, t, J=5.7 Hz, $CH_2$), 2.62 (2H, t, J=5.7 Hz, $CH_2$), 4.51 (2H, t, J=7 Hz, $CH_2$), m/z (ESP+) 241/243 (MH$^+$).

2-(4-Methoxyphenyl)-2,5,6,7,8,9-hexahydropyrazolo[4,3-c]cinnolin-3-one

4-Chloro-5,6,7,8-tetrahydrocinnoline-3-carboxylic acid ethyl ester (0.5 g), 4-methoxyphenylhydrazine hydrochloride (0.37 g) and potassium carbonate (0.29 g) in xylene were heated under reflux for 3 h. The solid was collected by filtration, washed with hexane, then water. The residue was absorbed onto silica and purified by flash chromatography using a gradient elution: $CH_2Cl_2$ (250 ml), $CH_2Cl_2$/(MeOH/$NH_3$ 10:1) 99:1 (250 ml), $CH_2Cl_2$/(MeOH/$NH_3$ 10:1) 98:2 (250 ml), $CH_2Cl_2$/(MeOH/$NH_3$ 10:1) 97:3 (250 ml), $CH_2Cl_2$/(MeOH/$NH_3$ 10:1) 96:4 (250 ml), $CH_2Cl_2$/(MeOH/$NH_3$ 10:1) 95:5 (250 ml). The appropriate fractions were combined and evaporated under reduced pressure to give a solid (79 mg, 13%). $\delta_H$ (360 MHz; DMSO) 1.83 (4H, m, $CH_2$), 2.67 (2H, t, J=5.3 Hz, $CH_2$), 2.72 (2H, d, J=5.3 Hz, $CH_2$), 3.78 (3H, s, $OCH_3$), 7.02 (2H, d, J=9 Hz, ArH), 8.06 (2H, d, J=9 Hz, $CH_2$), m/z (ESP+) 297 (MH$^+$).

EXAMPLE 2

2-(4-Fluorophenyl)-2,5,6,7,8,9-hexahydropyrazolo[4,3-c]cinnolin-3-one

4-Chloro-5,6,7,8-tetrahydrocinnoline-3-carboxylic acid ethyl ester (0.5 g), 4-fluorophenylhydrazine hydrochloride (0.34 g) and Hünig's base (0.73 ml) in xylene under nitrogen were heated under reflux for 2 h. The solid was collected by filtration, washed with diethyl ether, water and diethyl ether. The residue was recrystallised from ethanol to give the title compound (136 mg, 13%). $\delta_H$ (360 MHz; DMSO-$d_6$) 1.83 (4H, m, $CH_2$), 2.67 (2H, t, J=5.3 Hz, $CH_2$), 2.72 (2H, t, J=5.3 Hz, $CH_2$), 3.78 (3H, s, $OCH_3$), 7.02 (2H, d, J=9 Hz, ArH), 8.06 (2H, d, J=9 Hz, ArH), m/z (ESP+) 285 (MH$^+$). $C_{15}H_{13}FN_4O$ requires C, 63.37; H, 4.61; N, 19.71; found C, 62.96; H, 4.36; N, 19.48%.

EXAMPLE 3

2-(4-Methylphenyl)-2,5,6,7,8,9-hexahydropyrazolo[4,3-c]cinnolin-3-one

Using the procedure outlined in Example 2 the title compound was made. $\delta_H$ (360 MHz; DMSO-$d_6$) 1.83 (4H, m, $CH_2$), 2.33 (3H, s, $CH_3$), 2.67 (2H, t, J=5.5 Hz, $CH_2$), 2.75 (2H, t, J=5.3 Hz, $CH_2$), 7.26 (2H, d, J=9 Hz, ArH), 8.07 (2H, d, J=9 Hz, ArH), m/z (ESP+) 281 MH$^+$). $C_{16}H_{16}N_4O$ requires C, 68.55; H, 5.75; N, 19.99; found C, 68.60; H, 5.47; N, 19.89%.

EXAMPLE 4

2-(3-Chlorophenyl)-2,5,6,7,8,9-hexahydropyrazolo[4,3-c]cinnolin-3-one

Using the procedure outlined in Example 2 the title compound was made. $\delta_H$ (360 MHz; DMSO-$d_6$) 1.83 (4H, m, $CH_2$), 2.67 (2H, t, J=5.8 Hz, $CH_2$), 2.73 (2H, t, J=5.8 Hz, $CH_2$), 7.27 (1H, d, J=8 Hz, ArH), 7.48 (1H, t, J=8 Hz, ArH), 8.07 (1H, d, J=8 Hz, ArH), 8.17 (1H, t, J=8 Hz, ArH), m/z (ESP+) 300/302 (MH$^+$). $C_{15}H_{13}ClN_4O$ requires C, 59.90; H, 4.36; N, 18.63; found C, 59.82; H, 4.51; N, 18.11%.

EXAMPLE 5

2-(2-Fluorophenyl)-2,5,6,7,8,9-hexahydropyrazolo[4,3-c]cinnolin-3-one

4-Chloro-5,6,7,8-tetrahydrocinnoline-3-carboxylic acid ethyl ester (0.5 g), 2-fluorophenylhydrazine hydrochloride (0.34 g) and Hünig's base (0.73 ml) in xylene were heated under reflux for 3 h. The solvent was evaporated under reduced pressure and the residue purified by flash chromatography using a gradient elution: $CH_2Cl_2$ (500 ml), $CH_2Cl_2$/(MeOH/$NH_3$ 10:1) 99:1 (500 ml), $CH_2Cl_2$/(MeOH/$NH_3$ 10:1) 98:2 (500 ml), $CH_2Cl_2$/(MeOH/$NH_3$ 10:1) 97:3 (500 ml), $CH_2Cl_2$/(MeOH/$NH_3$ 10:1) 96:4 (500 ml), $CH_2Cl_2$/(MeOH/$NH_3$ 10:1) 95:5 (500 ml). The appropriate fractions were combined and evaporated under reduced pressure to give a solid (250 mg, 42%). $\delta_H$ (360 MHz; DMSO) 1.83 (4H, m, $CH_2$), 2.61 (2H, t, J=5.3 Hz, $CH_2$), 2.75 (2H, t, J=5.3 Hz, $CH_2$), 7.30–7.57 (4H, m, ArH), m/z (ESP+) 285 (MH$^+$). $C_{15}H_{13}FN_4O$ requires C, 63.37; H, 4.61; N, 19.71; found C, 63.18; H, 4.70; N, 19.35%.

EXAMPLE 6

2-(Pyridin-2-yl)-2,5,6,7,8,9-hexahydropyrazolo[4,3-c]cinnolin-3-one

Using the procedure outlined in Example 2 the title compound was made. $\delta_H$ (360 MHz; DMSO-$d_6$) 1.84 (4H, m, $CH_2$), 2.65 (2H, t, J=5.8 Hz, $CH_2$), 2.74 (2H, t, J=5.8 Hz, $CH_2$), 7.28 (1H, t, J=7 Hz, ArH), 7.89 (1H, t, J=7 Hz, ArH), 8.14 (1H, d, J=7 Hz, ArH), 8.50 (1H, d, J=7 Hz, ArH), m/z (ESP+) 268 (MH$^+$).

EXAMPLE 7

2-(4-Ethylphenyl)-2,5,6,7,8,9-hexahydropyrazolo[4,3-c]cinnolin-3-one

Using the procedure outlined in Example 2 the title compound was made. $\delta_H$ (360 MHz; DMSO-$d_6$) 1.20 (3H, t, J=7.5 Hz, $CH_3$), 1.83 (4H, m, $CH_2$), 2.51 (2H, q, J=7.5 Hz, $CH_2$), 2.66 (2H, t, J=5.8 Hz, $CH_2$), 2.73 (2H, t, J=5.8 Hz, $CH_2$), 7.28 (1H, d, J=8.5 Hz, ArH), 8.08 (1H, d, J=8.5 Hz, ArH), m/z (ESP+) 295 (MH$^+$).

EXAMPLE 8

2-(2,4-Difluorophenyl)-2,5,6,7,8,9-hexahydropyrazolo[4,3-c]cinnolin-3-one

Using the procedure outlined in Example 5 the title compound was made. $\delta_H$ (360 MHz; DMSO-$d_6$) 1.82 (4H, m, $CH_2$), 2.60 (2H, t, J=5.8 Hz, $CH_2$), 2.75 (2H, t, J=5.8 Hz, $CH_2$), 7.22 (1H, t, J=9 Hz, ArH), 7.46 (1H, t, J=9 Hz, ArH), 7.60 (1H, t, J=9 Hz, ArH), m/z (ESP+) 303 (MH$^+$).

EXAMPLE 9

2-(3,4-Dimethylphenyl)-2,5,6,7,8,9-hexahydropyrazolo[4,3-c]cinnolin-3-one

Using the procedure outlined in Example 5 the title compound was made. $\delta_H$ (360 MHz; DMSO-$d_6$) 1.83 (4H, m, $CH_2$), 2.24 (3H, s, $CH_3$), 2.28 (3H, s, $CH_3$), 2.67 (2H, t, J=5.8 Hz, $CH_2$), 2.75 (2H, t, J=5.8 Hz, $CH_2$), 7.19 (1H, d, J=8 Hz, ArH), 7.90 (1H, d, J=8 Hz, ArH), 7.95 (1H, s, ArH), m/z (ESP+) 295 (MH$^+$).

EXAMPLE 10

2-(3-Methylphenyl)-2,5,6,7,8,9-hexahydropyrazolo[4,3-c]cinnolin-3-one

Using the procedure outlined in Example 5 the title compound was made. $\delta_H$ (360 MHz; DMSO-$d_6$) 1.83 (4H, m, CH$_2$), 2.37 (3H, s, CH$_3$), 2.67 (2H, t, J=5.8 Hz, CH$_2$), 2.73 (2H, t, J=5.8 Hz, CH$_2$), 7.02 (H, d, J=7 Hz, ArH), 7.32 (1H, t, J=7 Hz, ArH), 7.99 (1H, s, ArH), 8.00 (1H, d, J=7 Hz, ArH), m/z (ESP+) 281 (MH$^+$).

EXAMPLE 11

2-(3-Fluorophenyl)-2,5,6,7,8,9-hexahydropyrazolo [4,3-c]cinnolin-3-one

Using the procedure outlined in Example 5 the title compound was made. δ$_H$ (360 MHz; DMSO-d$_6$) 1.83 (4H, m, CH$_2$), 2.67 (2H, t, J=5.8 Hz, CH$_2$), 2.73 (2H, t, J=5.8 Hz, CH$_2$), 7.04 (1H, m, ArH), 7.50 (1H, m, ArH), 8.04 (2H, m, ArH), m/z (ESP+) 285 (MH$^+$).

EXAMPLE 12

2-(4-Isopropylphenyl)-2,5,6,7,8,9-hexahydropyrazolo[4,3-c]cinnolin-3-one

Using the procedure outlined in Example 5 the title compound was made. δ$_H$ (360 MHz; DMSO-d$_6$) 1.21 (3H, s, CH$_3$), 1.23 (3H, s, CH$_3$), 1.83 (4H, m, CH$_2$), 2.67 (2H, t, J=5.8 Hz, CH$_2$), 2.73 (2H, t, J=5.8 Hz, CH$_2$), 2.73 (1H, m, CH), 7.31 (2H, d, J=8.6 Hz, ArH), 8.06 (2H, d, J=8.6 Hz, ArH), m/z (ESP+) 309 (MH$^+$).

EXAMPLE 13

2-(4-Ethoxy-phenyl)-2,5,6,7,8,9-hexahydropyrazolo [4,3-c]cinnolin-3-one

Using the procedure outlined in Example 5 the title compound was made. δ$_H$ (360 MHz; DMSO-d$_6$) 1.34 (3H, t, J=7 Hz, CH$_3$), 1.83 (4H, m, CH$_2$), 2.67 (2H, t, J=5.8 Hz, CH$_2$), 2.74 (2H, t, J=5.8 Hz, CH$_2$), 2.73 (H, m, CH), 7.31 (2H, d, J=8.6 Hz, ArH), 8.06 (2H, d, J=8.6 Hz, ArH), m/z (ESP+) 309 (MH$^+$).

EXAMPLE 14

2-(4-Chlorolphenyl)-2,5,6,7,8,9-hexahydropyrazolo [4,3-c]cinnolin-3-one 2-(4-Chlorophenyl)-2,5-dihydropyrazolo[4,3-c] cinnolin-3-one Prepared as described in U.S. Pat. No. 4,591,589.

2-(4-Chlorophenyl)-2,5,6,7,8,9-hexahydropyrazolo [4,3-c]cinnolin-3-one

To 2-(4-chlorophenyl)-2,5-dihydropyrazolo[4,3-c] cinnolin-3-one (0.5 g) dissolved in trifluoroacetic acid (20 ml) was added platinum oxide (0.2 g). The re action mixture was hydrogenated at 50 psi until no further uptake of hydrogen was observed. The catalyst was collected by filtration, the filtrate was poured onto ice and basified with ammonia. On the addition of dichloromethane a solid precipitated out; the solid was collected by filtration, washed with water and dried. Recrystallisation from ethanol gave the title compound. δ$_H$ (360 MHz; DMSO-d$_6$) 1.83 (4H, m, CH$_2$), 2.67 (2H, t, J=5.7 Hz, CH$_2$), 2.75 (2H, t, J=5.7 Hz, CH$_2$), 7.51 (2H, d, J=9 Hz, ArH), 8.23 (2H, d, J=9 Hz, ArH), m/z (ESP+) 301/303 (MH$^+$).

EXAMPLE 15

2-(4-Methoxyyhenyl)-2,5,6,7,8,9,10-heptahydrocyclohepta[c]pyrazolo[4,3-c]pyridazin-3-one 3-(2-Chlorocyclohept-1-enyl)-2-diazo-3-oxopropionic acid ethyl ester To a solution of 2-chlorocyclohept-1-enecarbonyl chloride (4.6 g) and ethyl diazoacetate (2.8 ml) in THF (30 ml) cooled to −70C was added a solution of lithium 2,2,6,6-tetramethylpiperidine (1 equiv.) dropwise. On completion of the addition the reaction mixture was stirred for 1 h. The reaction mixture was quenched by pouring into 1M citric acid (100 ml), then extracted with ether (3×200 ml). The ether extracts were combined, washed with brine, dried over magnesium sulphate, filtered and evaporated under reduced pressure to give an oil. The oil was purified by flash chromatography using a gradient elution: hexane/ether (10:1) 500 ml, hexane/ether (9:1) 500 ml, hexane/ether (8:2) 500 ml. The appropriate fractions were combined and evaporated under reduced pressure to give a yellow oil. δ$_H$ (360 MHz; CDCl$_3$) 1.33 (3H, t, J=7 Hz, CH$_3$), 1.74 (6H, m, CH$_2$), 2.32 (2H, m, CH$_2$), 2.64 (2H, m, CH$_2$), 4.29 (2H, t, J=7 Hz, CH$_2$).

4-Oxo-4,5,6,7,8,9-hexahydro-1H-cyclohepta[c]pyridazine-3-carboxylic acid ethyl ester To a solution of 3-(2-chlorocyclohept-1-enyl)-2-diazo-3-oxopropionic acid ethyl ester (1 g) in 1,4-dioxan (20 ml) was added a solution of tri-n-butylphosphine (1 ml) in 1,4-dioxan (10 ml). On completion of the addition the reaction mixture was stirred at room temperature for 30 minutes then heated to reflux for 2 h. The solvent was evaporated under reduced pressure and the residue purified by chromatography using a gradient elution: CH$_2$Cl$_2$ (250 ml), CH$_2$Cl$_2$/MeOH 99:1 (250 ml), CH$_2$Cl$_2$/MeOH 98:2 (250 ml), CH$_2$Cl$_2$/MeOH 97:3 (250 ml), CH$_2$Cl$_2$/MeOH 96:4 (250 ml). The appropriate fractions were combined and evaporated under reduced pressure to give a solid (360 mg, 41%). C$_{12}$H$_{16}$N$_2$O$_3$ requires C, 61.00; H, 6.83; N, 11.86. Found C, 60.80; H, 6.88; N, 11.84%. δ$_H$ (250 MHz; CDCl$_3$) 1.42 (3H, t, J=7 Hz, CH$_3$), 1.62 (2H, m, CH$_2$), 1.73 (2H, m, CH$_2$), 1.87 (2H, m, CH$_2$), 2.86 (2H, m, CH$_2$), 3.09 (2H, m, CH$_2$), 4.48 (2H, t, J=7 Hz, CH$_2$), m/z (ESP+) 237 (MH$^+$).

4-Chloro-6,7,8,9-tetrahydro-5H-cyclohepta[c]pyridazine-3-carboxylic acid ethyl ester To a solution of 4-oxo-4,5,6,7,8,9-hexahydro-1H-cyclohepta[c]pyridazine-3-carboxylic acid ethyl ester (2.7 g) and pyridine (0.93 ml) in dichloromethane (150 ml) was added p-toluenesulphonyl chloride (2.2 g). The reaction mixture was heated at reflux for 20 h. The reaction mixture was washed with 1M potassium carbonate solution, brine, dried over magnesium sulphate, filtered and evaporated under reduced pressure to give an oil. The oil was purified by flash chromatography using a gradient elution: CH$_2$Cl$_2$ (500 ml), CH$_2$Cl$_2$/MeOH 99:1 (500 ml), CH$_2$Cl$_2$/MeOH 98:2 (500 ml), CH$_2$Cl$_2$/MeOH 97:3 (500 ml), CH$_2$Cl$_2$/MeOH 96:4 (500 ml). The appropriate fractions were combined and evaporated under reduced pressure to give a solid (0.65 g, 22%). C$_{12}$H$_{15}$ClN$_2$O$_2$ requires C, 56.58; H, 5.93; N, 11.00. Found C, 56.52; H, 6.06; N, 11.01%. δ$_H$ (360 MHz; CDCl$_3$) 1.44 (3H, t, J=7 Hz, CH$_3$), 1.70 (2H, m, CH$_2$), 1.77 (2H, m, CH$_2$), 1.92 (2H, m, CH$_2$), 3.06 (2H, m, CH$_2$), 3.32 (2H, m, CH$_2$), 4.51 (2H, t, J=7 Hz, CH$_2$), m/z (ESP+) 255/257 (MH$^+$).

2-(4-Methoxyphenyl)-2,5,6,7,8,9,10-heptahydrocyclohepta[c]pyrazolo[4,3-c]pyridazin-3-one 4-Chloro-6,7,8,9-tetrahydro-5H-cyclohepta[c]pyridazine-3-carboxylic acid ethyl ester (0.25 g), 4-methoxyphenylhydrazine hydrochloride (0.17 g) and Hünig's base (0.34 ml) in xylene (10 ml) were heated under reflux for 4 h. The solid was collected by filtration, washed with hexane and dried. The solid was partitioned between dichloromethane and water, the dichloromethane extracts were combined, dried over magnesium sulphate, filtered and evaporated under reduced pressure to give a solid. 8H (360 MHz; DMSO-$d_6$) 1.66 (4H, m, $CH_2$), 1.86 (2H, m, $CH_2$), 2.88 (2H, m, $CH_2$), 2.93 (2H, m, $CH_2$), 3.78 (3H, s, $OCH_3$), 7.02 (2H, d, J=9 Hz, ArH), 8.10 (2H, d, J=9 Hz, ArH), m/z (ESP+) 311 ($MH^+$).

EXAMPLE 16

2-(4-Methylphenyl)-2,5,6,7,8,9,10-heptahydrocyclohepta[c]pyrazolo[4,3-c]pyridazin-3-one 4-Chloro-6,7,8,9-tetrahydro-5H-cyclohepta[c]pyridazine-3-carboxylic acid ethyl ester (0.25 g), 4-methylphenylhydrazine hydrochloride (0.17 g) and Hünig's base (0.34 ml) in xylene (10 ml) were heated under reflux for 5 h. The solvent was evaporated under reduced pressure. The residue was partitioned between ethyl acetate and water, the solid which precipitated out was collected by filtration, washed with water, then ether and dried. $\delta_H$ (360 MHz; DMSO-$d_6$) 1.66 (4H, m, $CH_2$), 1.86 (2H, m, $CH_2$), 2.33 (2H, s, $CH_3$), 2.88 (2H, m, $CH_2$), 2.94 (2H, m, $CH_2$), 7.25 (2H, d, J=9 Hz, ArH), 8.10 (2H, d, J=9 Hz, ArH), m/z (ESP+) 295 ($MH^+$).

EXAMPLE 17

2-(4-Chlorophenyl)-2,5,6,7,8,9,10-heptahydrocyclohepta[c]pyrazolo[4,3-c]pyridazin-3-one 4-Chloro-6,7,8,9-tetrahydro-5H-cyclohepta[c]pyridazine-3-carboxylic acid ethyl ester (0.25 g), 4-chlorophenylhydrazine hydrochloride (0.18 g) and Hünig's base (0.34 ml) in xylene (10 ml) were heated under reflux for 3 h. The solvent was evaporated under reduced pressure and the residue purified by flash chromatography using a gradient elution: $CH_2Cl_2$ (250 ml), $CH_2Cl_2$/MeOH 99:1 (250 ml), $CH_2Cl_2$/MeOH 98:2 (250 ml), $CH_2Cl_2$/MeOH 97:3 (250 ml), $CH_2Cl_2$/MeOH 96:4 (250 ml). The appropriate fractions were combined and evaporated under reduced pressure to give a solid (53 mg, 17%). $\delta_H$ (360 MHz; DMSO-$d_6$) 1.66 (4H, m, $CH_2$), 1.86 (2H, m, $CH_2$), 2.88 (2H, m, $CH_2$), 2.94 (2H, m, $CH_2$), 7.51 (2H, d, J=9 Hz, ArH), 8.27 (2H, d, J=9 Hz, ArH), m/z (ESP+) 315 ($MH^+$). $C_{16}H_{15}ClN_4O$ requires C, 61.05; H, 4.80; N, 17.80. Found C, 60.75; H, 4.54; N, 17.54%.

EXAMPLE 18

2-(4-Fluorophenyl)-2,5,6,7,8,9,10-heptahydrocyclohepta[c]pyrazolo[4,3-c]pyridazin-3-one Using the procedure as shown in Example 17 the title compound was obtained. $\delta_H$ (360 MHz; DMSO-$d_6$) 1.66 (4H, m, $CH_2$), 1.86 (2H, m, $CH_2$), 2.88 (2H, m, $CH_2$), 2.94 (2H, m, $CH_2$), 7.29 (2H, t, J=9 Hz, ArH), 8.24 (2H, m, ArH), m/z (ESP+) 299 ($MH^+$).

EXAMPLE 19

2-(3-Methoxyphenyl)-2,5,6,7,8,9,10-heptahydrocyclohepta[c]pyrazolo[4,3-c]pyridazin-3-one Using the procedure as shown in Example 17 the title compound was obtained. $\delta_H$ (360 MHz; DMSO-$d_6$) 1.66 (4H, m, $CH_2$), 1.86 (2H, m, $CH_2$), 2.88 (2H, m, $CH_2$), 2.92 (2H, m, $CH_2$), 3.80 (3H, s, $OCH_3$), 6.79 (1H, d, J=8 Hz, ArH), 7.35 (1H, t, J=8 Hz, ArH), 7.82 (1H, d, J=8 Hz, ArH), 8.87 (1H, s, ArH), m/z (ESP+) 311 ($MH^+$). $C_{17}H_{18}N_4O_2$ requires C, 65.79; H, 5.85; N, 18.05. Found C, 66.07; H, 5.73; N, 17.77%.

EXAMPLE 20

2-(Pyridin-2-yl)-2,5,6,7,8,9,10-heptahydrocyclohepta[c]pyrazolo[4,3-c]pyridazin-3-one Using the procedure as shown in Example 17 the title compound was obtained. $\delta_H$ (360 MHz; DMSO-$d_6$) 1.66 (4H, m, $CH_2$), 1.86 (2H, m, $CH_2$), 2.88 (2H, m, $CH_2$), 2.93 (2H, m, $CH_2$), 7.28 (1H, m, ArH), 7.90 (1H, t, J=8 Hz, ArH), 8.16 (1H, d, J=8 Hz, ArH), 8.54 (1H, d, J=8 Hz, ArH), m/z (ESP+) 282 ($MH^+$).

EXAMPLE 21

2-(4-Methylpyridin-2-yl)-2,5,6,7,8,9,10-heptahydrocyclohepta[d]pyrazolo-[4,3-c]pyridazin-3-one Using the procedure as shown in Example 17 the title compound was obtained. $\delta_H$ (360 MHz; DMSO-$d_6$) 1.65 (4H, m, $CH_2$), 1.86 (2H, m, $CH_2$), 2.33 (3H, s, $CH_3$), 2.87 (2H, m, $CH_2$), 2.93 (2H, m, $CH_2$), 7.73 (1H, d, J=8 Hz, ArH), 8.04 (1H, d, J=8 Hz, ArH), 8.34 (1H, s, ArH), m/z (ESP+) 296 ($MH^+$). $C_{16}H_{17}N_5O$ requires C, 65.07; H, 5.80; N 23.71. Found C, 65.10; H, 5.75; N, 23.49%.

What is claimed is:

1. A compound of formula I, or a salt or prodrug thereof:

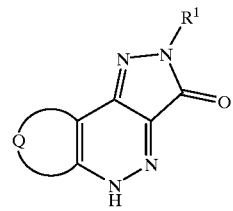

(I)

wherein

Q represents —$(CH_2)_n$—;

n is 3, 4, 5 or 6; and $R^1$ represents aryl or heteroaryl, either of which groups may be optionally substituted.

2. A compound as claimed in claim 1 represented by formula II, and salts and prodrugs thereof:

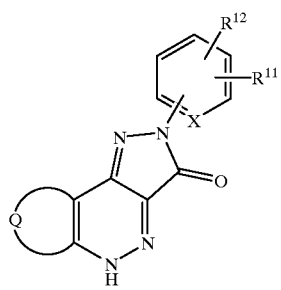

(II)

wherein

Q is as defined in claim 1;

X represents CH or nitrogen; and $R^{11}$ and $R^{12}$ independently represent hydrogen, $C_{1-6}$ alkyl, $C_{1-6}$ alkoxy, $C_{1-6}$ alkylsulphonyl, $C_{2-6}$ alkylcarbonyl, halogen, cyano or trifluoromethyl.

3. A compound as claimed in claim 1 wherein Q represents —$(CH_2)_n$— in which n is 4 or 5.

4. A compound as claimed in claim 2 wherein $R^{11}$ represents hydrogen, $C_{1-6}$ alkyl, $C_{1-6}$ alkoxy or halogen.

5. A compound as claimed in claim 2 wherein $R^{12}$ represents hydrogen, $C_{1-6}$ alkyl or halogen.

6. A compound selected from:

2-(4-methoxyphenyl)-2,5,6,7,8,9-hexahydropyrazolo[4,3-c]cinnolin-3-one;

2-(4-fluorophenyl)-2,5,6,7,8,9-hexahydropyrazolo[4,3-c]cinnolin-3-one;

2-(4-methylphenyl)-2,5,6,7,8,9-hexahydropyrazolo[4,3-c]cinnolin-3-one;

2-(3-chlorophenyl)-2,5,6,7,8,9-hexahydropyrazolo[4,3-c]cinnolin-3-one;

2-(2-fluorophenyl)-2,5,6,7,8,9-hexahydropyrazolo[4,3-c]cinnolin-3-one;

2-(pyridin-2-yl)-2, 5,6,7,8,9-hexahydropyrazolo[4,3-c]cinnolin-3-one;

2-(4-ethylphenyl)-2,5,6,7,8,9-hexahydropyrazolo[4,3-c]cinnolin-3-one;

2-(2,4-difluorophenyl)-2,5,6,7,8,9-hexahydropyrazolo[4,3-c]cinnolin-3-one;

2-(3,4-dimethylphenyl)-2,5,6,7,8,9-hexahydropyrazolo[4,3-c]cinnolin-3-one;

2-(3-methylphenyl)-2,5,6,7,8,9-hexahydropyrazolo[4,3-c]cinnolin-3-one;

2-(3-fluorophenyl)-2,5,6,7,8,9-hexahydropyrazolo[4,3-c]cinnolin-3-one;

2-(4-isopropylphenyl)-2,5,6,7,8,9-hexahydropyrazolo[4,3-c]cinnolin-3-one;

2-(4-ethoxyphenyl)-2,5,6,7,8,9-hexahydropyrazolo[4,3-c]cinnolin-3-one;

2-(4-chlorophenyl)-2,5,6,7,8,9-hexahydropyrazolo[4,3-c]cinnolin-3-one;

2-(4-methoxyphenyl)-2,5,6,7,8,9,10-heptahydrocyclohepta[c]pyrazolo[4,3-c]pyridazin-3-one;

2-(4-methylphenyl)-2,5,6,7,8,9,10-heptahydrocyclohepta[c]pyrazolo[4,3-c]pyridazin-3-one;

2-(4-chlorophenyl)-2,5,6,7,8,9,10-heptahydrocyclohepta[c]pyrazolo[4,3-c]pyridazin-3-one;

2-(4-fluorophenyl)-2,5,6,7,8,9,10-heptahydrocyclohepta[c]pyrazolo[4,3-c]pyridazin-3-one;

2-(3-methoxyphenyl)-2,5,6,7,8,9,10-heptahydrocyclohepta[c]pyrazolo[4,3-c]pyridazin-3-one;

2-(pyridin-2-yl)-2,5,6,7,8,9,10-heptahydrocyclohepta[c]pyrazolo[4,3-c]pyridazin-3-one;

2-(4-methylpyridin-2-yl)-2,5,6,7,8,9,10-heptahydrocyclohepta[c]pyrazolo-[4,3-c]pyridazin-3-one;

and salts and prodrugs thereof.

7. A pharmaceutical composition comprising a compound of formula I as defined in claim 1 or a pharmaceutically acceptable salt thereof or a prodrug thereof in association with a pharmaceutically acceptable carrier.

8. A method for the treatment of anxiety which comprises administering to a patient in need of such treatment an effective amount of a compound of formula I as defined in claim 1, or a pharmaceutically acceptable salt thereof or a prodrug thereof.

9. A method for the treatment of convulsions which comprises administering to a patient in need of such treatment an effective amount of a compound of formula I as defined in claim 1, or a pharmaceutically acceptable salt thereof or a prodrug thereof.

\* \* \* \* \*